US012633404B2

(12) United States Patent (10) Patent No.: US 12,633,404 B2
Roser et al. (45) Date of Patent: May 19, 2026

(54) METHOD AND SYSTEM FOR MONITORING A ROOM HAVING A MEDICAL TECHNOLOGY APPARATUS

(71) Applicant: Siemens Healthineers AG, Forchheim (DE)

(72) Inventors: Philipp Roser, Erlangen (DE); Marcus Pfister, Bubenreuth (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/779,076

(22) Filed: Jul. 21, 2024

(65) Prior Publication Data

US 2025/0029712 A1 Jan. 23, 2025

(30) Foreign Application Priority Data

Jul. 21, 2023 (DE) ..................... 10 2023 206 963.6

(51) Int. Cl.
G16H 40/20 (2018.01)
G16H 40/40 (2018.01)
(52) U.S. Cl.
CPC ............. G16H 40/20 (2018.01); G16H 40/40 (2018.01)
(58) Field of Classification Search
CPC ........ G16H 40/20; G16H 40/40; G08B 21/02; G01B 11/00; G01V 8/10
See application file for complete search history.

(56) References Cited

U.S. PATENT DOCUMENTS

| | | | | |
|---|---|---|---|---|
| 5,600,487 | A | * | 2/1997 | Kiyomoto ............ G02B 6/4246 |
| | | | | 359/586 |
| 2008/0258929 | A1 | | 10/2008 | Maschke |
| 2009/0073405 | A1 | | 3/2009 | Kanaya |
| 2013/0003915 | A1 | | 1/2013 | Lautenschlager et al. |
| 2013/0201292 | A1 | | 8/2013 | Walter |
| 2017/0071558 | A1 | | 3/2017 | Hoornaert et al. |

(Continued)

FOREIGN PATENT DOCUMENTS

| | | |
|---|---|---|
| CN | 110476079 A | 11/2019 |
| CN | 211067858 U | 7/2020 |

(Continued)

OTHER PUBLICATIONS

Abidi, et. al. "Survey and Analysis of Multimodal Sensor Planning and Integration for Wide Area Surveillance." ACM Computing Surveys, vol. 41, No. 1, Article 7, Publication date: Dec. 2008 (Year: 2008).*

(Continued)

*Primary Examiner* — Linh Giang Le
(74) *Attorney, Agent, or Firm* — Lempia Summerfield Katz LLC

(57) ABSTRACT

For monitoring a room with a medical technology apparatus, a light projection that defines an areal region in the room is generated with light of a predetermined wavelength characteristic. Using a large number of optical detectors that are each mounted in the areal region and are configured for detecting light having the wavelength characteristic, at least one detector signal is generated. Dependent upon the at least one detector signal, a coverage of at least a portion of the large number of optical detectors by an object is recognized. Dependent upon the recognized coverage, a safety and/or warning measure is initiated.

15 Claims, 2 Drawing Sheets

(56)     References Cited

U.S. PATENT DOCUMENTS

| 2019/0018382 A1 | 1/2019 | Elkmann | |
|---|---|---|---|
| 2020/0096635 A1 | 3/2020 | Fischer et al. | |
| 2022/0334400 A1* | 10/2022 | Ott | G02B 27/4255 |

FOREIGN PATENT DOCUMENTS

| DE | 102006011249 A1 | | 2/2009 |
|---|---|---|---|
| DE | 102015215234 A1 | | 2/2017 |
| EP | 2558886 B1 | | 3/2014 |
| JP | 08029542 A | * | 9/1994 |
| JP | H08293396 A | | 11/1996 |
| JP | 2007243004 A | | 9/2007 |
| WO | 2019101868 A1 | | 5/2019 |

OTHER PUBLICATIONS

German Decision to Grant for Application No. 10 2023 206 963.6 mailed Feb. 10, 2025, with English translation.

German Office Action for Application No. 10 2023 206 963.6 mailed Mar. 6, 2024, with English translation.

Jeseno, "Industrial Floor Markings" Obtained https://www.jeseno.de/bodenmarkierungen/ [status of Jun. 27, 2024]. pp. 1-33, with English translation.

Joom, "Laser Alarm System Infrared Beam Sensor Motion Detector Outdoor Home Security" Obtained https://www.joom.com/de/products/5d6e2e1d8b45130101ebb454 [status: Jun. 27, 2024]; pp. 1-7.

* cited by examiner

METHOD AND SYSTEM FOR MONITORING A ROOM HAVING A MEDICAL TECHNOLOGY APPARATUS

This application claims the benefit of German Patent Application No. DE 10 2023 206 963.6, filed on Jul. 21, 2023, which is hereby incorporated by reference in its entirety.

BACKGROUND

The present embodiments relate to a method for monitoring a room having a medical technology apparatus and a corresponding system for monitoring a room.

When medical technology apparatuses are utilized, for example, for medical imaging and/or for carrying out medical interventions (e.g., minimally invasive interventions, such as with imaging support), occasionally complex sequences and movements of the medical technology apparatuses or other objects in the room are required. If, for example, persons are present in a movement region of the medical technology apparatus, then collisions, accidents, and injuries may occur. It is therefore sometimes desirable that persons active in the room avoid the relevant regions. The same may also apply similarly for pre-defined sterile regions or regions with a potentially elevated radiation burden.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a reliable possibility for monitoring a room having a medical technology apparatus is provided.

Underlying the present embodiments is the concept of defining, by light projection with light of a pre-determined wavelength characteristic, an areal region in the room, and, using a large number of optical detectors, detecting light with the wavelength characteristic in the areal region to recognize a coverage by an object. Dependent upon the recognized coverage, a safety and/or warning measure is initiated.

According to one aspect of the present embodiments, a method for monitoring a room is provided, where the room contains a medical technology apparatus and/or a medical technology apparatus is arranged in the room. For example, using a light projection apparatus mounted in the room, a light projection that defines an areal region in the room is generated with light of a pre-determined wavelength characteristic. Using a large number of optical detectors that are each mounted in the areal region and are configured for detecting light having the wavelength characteristic, at least one detector signal is generated. Dependent upon the at least one detector signal (e.g., by at least one computing unit), a coverage of at least a portion of the large number of optical detectors by an object is recognized, and, dependent upon the recognized coverage, a safety and/or warning measure is initiated.

For example, the safety and/or warning measure is initiated and carried out dependent upon the recognized coverage.

A medical technology apparatus may be any desired technical apparatus for, for example, at least partial automatic execution of a diagnostic, therapeutic, surgical, and/or imaging procedure. The execution of a diagnostic, therapeutic, and/or surgical procedure, however, cannot be regarded as a constituent part of the method according to the present embodiments.

The medical technology apparatus may include, for example, an imaging modality such as an ultrasonic imaging system, an X-ray based imaging system (e.g., a C-arm angiography system or a CT system), or a magnetic resonance tomography system. The medical technology apparatus may also include an apparatus for carrying out therapeutic procedures, such as a high intensity focused ultrasound (HIFU) system or a histotripsy system and suchlike. The medical technology apparatus may also include accessories such as measuring facilities, electrical lines, or hoses and so forth for a system of this type.

Here and in the following, the expression "light" may be electromagnetic waves in the visible region, in the infrared region, and/or in the ultraviolet region. Accordingly, the expression "optical" may also relate to light in accordance with this understanding.

In one embodiment, the light is generated at least partially in the visible spectral region. Accordingly, persons who are present in, or move within, the room may visually recognize the light projection and, where relevant, avoid the areal region.

The light projection may define the areal region in various ways. For example, the light projection may illuminate the areal region completely, or one or more contours of the areal region. It is also possible that an areal subregion of the areal region is illuminated by the light projection in order to define the areal region. The areal subregion may correspond, for example, to a pre-determined region about one or more contours of the areal region.

The wavelength characteristic is defined, for example, via a wavelength spectrum of the light generated via the light projection apparatus. The wavelength characteristic may be identical to the wavelength spectrum or may include one or more properties of the wavelength spectrum (e.g., maximum sites or suchlike). If the light projection apparatus is, for example, a laser projection apparatus, the wavelength characteristic may correspond, for example, to an emission wavelength of one or more corresponding laser light sources of the laser projection apparatus.

The wavelength characteristic may also be given by a wavelength region or a plurality of wavelength regions within which the relative amplitude of the emitted light is greater than a pre-determined threshold value. It is also possible that the light projection apparatus has one or more optical filters in order to filter the light generated by one or more suitable light sources of the light projection apparatus. The wavelength characteristic is then, for example, a wavelength characteristic of the filtered light. Thus, for example, a wavelength band of a corresponding band-pass filter or suchlike may serve as the wavelength characteristic.

The optical detectors of the large number of optical detectors are each configured to detect light with the wavelength characteristic. In other words, the optical detectors are adjusted, for example, to the wavelength characteristic. This may take place, for example, by a corresponding selection of materials used in the optical detectors (e.g., if the optical detectors are photodiodes or suchlike) and/or via a corresponding light filtration of the light falling on the plurality of optical detectors.

For example, it can be the case that a sensitivity of the optical detectors to light that does not correspond to the wavelength characteristic is less than a sensitivity to light corresponding to the wavelength characteristic. For example, therefore, it may be achieved that the optical detectors only detect light having the wavelength characteristic or that a sensitivity of the optical detectors to light with the wavelength characteristic is elevated as compared with other light.

For example, the wavelength characteristic and the optical detectors may correspondingly be configured such that, apart from the light projection apparatus, no further light sources in the room that may, in principle, illuminate the areal region generate light with the wavelength characteristic. It may thus be achieved with greater reliability that the optical detectors are actually able to detect the light projection and may, accordingly, reliably detect the coverage.

Via a corresponding adaptation of the wavelength characteristic in relation to the other light sources, as mentioned, it may be achieved, for example, that the coverage is recognized as coverage in relation to the light projection of the light projection apparatus, even if possibly other light sources illuminate the areal region with a different wavelength characteristic.

For example, each optical detector generates one of the at least one detector signals, dependent upon light detected by this optical detector (e.g., dependent upon the light that is incident upon an active surface of the corresponding optical detector, such as dependent upon a light energy imparted by the light). The number of detector signals of the at least one detector signal then corresponds therefore to the number of optical detectors in the large number of optical detectors.

The coverage by the object may therefore not only be recognized in principle, but may also be localized by identifying the individual covered optical detectors within the areal region. Therefore, in other words, the portion of the areal region that is covered by the object may be determined. For example, in some embodiments, the safety and/or warning measure may be initiated dependent upon which portion of the areal region is covered by the object.

The safety and/or warning measure is, for example, only initiated, for example, precisely when the coverage has been recognized or when the coverage has been recognized in a predefined portion of the areal region and/or when additional conditions are met. The additional conditions may include, for example, a temporal change in the coverage or in the position of the coverage. For example, the safety and/or warning measure may be initiated dependent upon whether the object moves according to the detected coverage and/or in which direction it moves.

It is also possible that the safety and/or warning measure is initiated when the coverage is not recognized or is not recognized in a particular portion of the areal region although, for example according to a pre-determined room model, a coverage is expected there (e.g., because the medical technology apparatus or another object in the room should be so positioned that a corresponding coverage results).

It is also possible that the corresponding conditions for initiating the safety and/or warning measure change over time. For example, at different time points, different conditions are required to initiate the safety and/or warning measure. Accordingly, at different time points or time periods during an imaging method or a medical intervention, different reactions may take place. This is, for example, advantageous if an elevated radiation burden is to be expected in the areal region only during particular time periods, and not outside these time periods. Accordingly, the safety and/or warning measure may be initiated, for example, only during the corresponding time region or time period or suchlike.

Via the method according to the present embodiments, it is made possible to monitor the room such that given an undesired presence of the object in the areal region or an undesired absence of the object in the areal region, the safety and/or warning measure may be initiated. The safety and/or warning measure then leads, where relevant, to the reduction of a risk of a collision of the object with a component (e.g., a movable component), the medical technology apparatus, or another object in the room and/or to a reduced radiation burden on a person if the object is a person, and/or an avoidance of an entry into sterile regions and so forth. The adaptation of the optical detectors to the wavelength characteristic may, first, increase the reliability of the method and, second, prevent false positive detections of the coverage.

In contrast, for example, to a monitoring of the room by camera, the method according to the present embodiments does not necessarily require the detection or processing of person-specific data. This may be advantageous considered from the standpoint of data protection.

In some embodiments, the areal region is a region on a base or a floor or a floor area of the room. In some embodiments, the light projection apparatus is mounted on a ceiling or a side wall of the room.

According to at least one embodiment, the safety and/or warning measure includes a stopping or braking of a movement of a component of the medical technology apparatus.

The areal region is therefore, for example, a movement region of the component (e.g., a region in which a collision of the component with the object potentially threatens if the object is in the areal region or covers the areal region).

Accordingly, by way of the stopping or braking of the movement of the component, the risk of the collision may be lessened.

According to at least one embodiment, the safety and/or warning measure includes a cessation of a generation of ionizing radiation by the medical technology apparatus.

In a regular operation, for example, ionizing radiation is generated by the medical technology apparatus (e.g., to carry out an imaging procedure). For example, in such embodiments, the medical technology apparatus includes an X-ray source by which the ionizing radiation (e.g., X-ray radiation) is generated.

The areal region is, for example, a region of elevated radiation burden due to the ionizing radiation. Via the cessation of the generation of the ionizing radiation, therefore, the risk to a person of an elevated radiation burden may be reduced.

According to at least one embodiment, the safety and/or warning measure includes a bringing of the component or a further component of the medical technology apparatus into a predefined safe position or a safe location.

A location may be understood here and in the following to be the combination of a position with a corresponding orientation or alignment in the three-dimensional space.

Also, via the bringing of the component into the predefined safe position or location, the risk of a collision with the object may be reduced.

In various embodiments, for example, initially, the movement of the component may be stopped or braked, and the components may then be brought into a safe position or location.

According to at least one embodiment, the safety and/or warning measure includes an output of an acoustic warning message and/or a visual warning message.

The acoustic warning message may be generated and output, for example, by a loudspeaker apparatus that is mounted in the room. For example, the loudspeaker apparatus may also include a plurality of loudspeakers that are driven by the at least one computing unit such that the acoustic warning message is generated in a spatially limited manner in a target region or is suppressed outside the target region. The target region may correspond to the surface region or a portion thereof or a surrounding region of the areal region or the areal region including a pre-determined vicinity.

The acoustic warning message may, however, also be generated and output by a mobile electronic device that a person who, in this case, for example, represents the object wears or carries. For example, the acoustic warning message may be generated by a smartphone or a pager or some other receiver that is in wireless communication with the at least one computing unit.

The visual warning message may similarly also be generated and output by an illumination apparatus arranged in the room and/or by the mobile electronic device and/or by a display or a monitor in the room.

By this, a flexible and diverse informing and warning of the relevant persons who enter undesirably into the areal region or are about to do so, or of other persons in the room, may be enabled.

For example, via the person-specific warning by the acoustic and/or visual warning message on the mobile electronic device, it may be achieved that the warning is issued only for particular person groups or persons. Thus, it may be desired or required that particular groups of persons enter a particular region although this may possibly result in an elevated radiation dose, or suchlike.

According to at least one embodiment, a form and/or a size and/or a position of the areal region in the room is changed (e.g., tracked) dependent upon a state of the medical technology apparatus.

The state may be, for example, a movement state of a movable component of the medical technology apparatus (e.g., thus, a momentary position or location of the movable component).

On a change in the state of the medical technology apparatus, the position and/or the shape and/or size of the region in which an elevated collision risk exists and/or in which an elevated radiation burden is to be feared also possibly changes. Via corresponding adaptation of the areal region (e.g., by the light projection apparatus), the areal region may be tracked accordingly. This has the consequence that the size of the areal region may be reduced.

In such embodiments, the optical detectors of the large number of optical detectors are distributed in the room, for example, such that both before as well as after the change in the position and/or shape and/or size of the areal region, a corresponding portion of the large number of optical detectors is always arranged within the areal region.

According to at least one embodiment, dependent upon the at least one detector signal, a movement of the object is detected, for example, by the at least one computing unit. The safety and/or warning measure is initiated dependent upon the detected movement.

The movement is detected, for example, in that the temporal sequence of the optical detectors of the large number of optical detectors that are covered by the object is evaluated. In this way, it may be determined, for example, whether the object moves in the areal region and possibly also in which direction. For example, the safety and/or warning measure may be initiated only when the object moves, so that static objects may be categorized as not critical.

It is also possible that the safety and/or warning measure is only initiated when the object moves in a particular direction or only when the object does not move in a particular direction. Thus, for example, the initiation of the safety and/or warning measure may be restricted to relevant scenarios in which the object does not in any case already leave correspondingly critical regions in which the object is in the process of moving in the direction of particularly critical regions, and so forth.

According to at least one embodiment, the safety and/or warning measure is initiated if (e.g., only if) it is ascertained, based on the detected movement, that the object moves in the direction of a predetermined critical region.

The critical region may therein be inside or outside the areal region or may be partially inside the areal region. In this way, unnecessary warnings or safety measures may be avoided.

According to at least one embodiment, a room model (e.g., a virtual room model of the room) is provided, for example, to the at least one computing unit (e.g., by storing the room model on a computer-readable storage medium). The safety and/or warning measure is initiated dependent upon the room model.

The room model may include, for example, information about where in the room the medical apparatus or individual components of the medical apparatus or other apparatuses and objects, including walls, etc., of the room are situated. The room model may also include information regarding dynamic processes (e.g., the movement of one or more components of the medical technology apparatus or other apparatuses in the room) or a corresponding description of such movements. The room model may also include typical movements or movement sequences of persons in the room, including medical personnel and possibly patients.

In this way, when the safety and/or warning measure is initiated, for example, a target state and/or uncritical states in the room may be taken into account, so that in instances of coverage of the areal region or portions of the areal region that are to be expected and/or possibly desired, according to the room model, no safety and/or warning measure is initiated, and so forth.

According to at least one embodiment, the room model includes a position or location of the medical technology apparatus and/or a further object in the room. The safety and/or warning measure is initiated dependent upon the position or location of the medical technology apparatus and/or of the at least one further object.

According to at least one embodiment, the room model includes a movement region of the medical technology apparatus (e.g., the movable component of the medical technology apparatus and/or of the at least one further object). The safety and/or warning measure is initiated dependent upon the movement region of the medical technology apparatus and/or of the at least one further object.

According to at least one embodiment, dependent upon the recognized coverage, a sensor that is arranged in the areal region or in a predetermined further areal region in the room is activated. Using the sensor, a sensor signal is generated dependent upon a presence of the object in a detection region of the further sensor. The safety and/or warning measure is initiated dependent upon the sensor signal.

For example, the safety and/or warning measure may be initiated only when, according to the sensor signal, the presence of the object in the detection region is ascertained.

The sensor may be, for example, a pressure sensor that is integrated into a floor or base of the room. The sensor may also be an induction sensor or a magnetic field sensor and suchlike. It is also possible to provide one or more further sensors of the same type or a different type and to initiate the safety and/or warning measure dependent upon corresponding sensor signals from the individual sensors.

In this way, therefore, initially, based on the coverage of one or more of the optical detectors, the presence of the object may be recognized, and in a second act, the presence of the object in the detection region may also recognized by the sensor. Thus, for example, a more reliable recognition of the object may be achieved, and/or the risk of a false positive detection of the object in the areal region may be reduced. Possibly, also a more exact position determination of the object based upon the sensor signal is possible, so that dependent upon the position thus determined, the safety and/or warning measure may be initiated.

According to at least one embodiment, light incident upon the large number of optical detectors is filtered according to the wavelength characteristic (e.g., by a filter apparatus arranged in the room).

The filter apparatus may be arranged, for example, in the areal region, such that light that reaches the active surfaces of the individual optical detectors has previously necessarily passed through the filter apparatus. Therein, each optical detector may have its own filter element or a plurality of optical detectors (e.g., all the optical detectors of the large number of optical detectors) may each have shared filter elements.

In this way, as described above, the adaptation of the optical detectors or of the detected light portions to the wavelength characteristic may be improved.

The filter apparatus may, for example, be configured such that the at least one portion of the light with the wavelength characteristic may be transmitted and/or only light according to the wavelength characteristic may be transmitted.

According to at least one embodiment, the areal region corresponds to a movement region or the movement region of the medical apparatus (e.g., the component of the medical apparatus).

In this way, a risk of collision with the object may be reduced.

According to at least one embodiment, the areal region corresponds to a region of elevated radiation burden (e.g., from the medical technology apparatus).

In this way, the risk of an elevated radiation burden on persons in the room may be reduced.

According to at least one embodiment, the areal region corresponds to a pre-determined sterile region in the room.

In this way, the sterility of the sterile region may be provided more reliably.

According to at least one embodiment, the identity of the object is ascertained (e.g., by the at least one computing unit), and the safety and/or warning measure is initiated dependent upon the ascertained identity.

For the ascertaining of the identity, for example, a camera system may be provided in the room. The camera may monitor the room and thereby persons and other objects in the room. Dependent upon corresponding camera images or videos of the camera system, using known algorithms, for example, facial recognition algorithms, etc., the at least one computing unit may ascertain the identity of the object (e.g., a person).

In other embodiments, additionally or alternatively thereto, the identity of the object may be determined by reading out corresponding identification information from an RFID track of the object using a corresponding RFID reading device.

By this, for example, the safety and/or warning measure may only be initiated if the object is an object of a particular identity or a particular group (e.g., a particular group of persons). Thus, the unnecessary initiation of safety and/or warning measures may be further reduced.

For application cases or application situations that may arise with a method according to the present embodiments and are not explicitly described here, it may be provided that according to the method, an error message and/or a request for input of a user feedback is output, and/or a standard setting and/or a predetermined initial state is set.

According to a further aspect of the present embodiments, a system for monitoring a room having at least one medical technology apparatus is provided. The system has a light projection apparatus for mounting in the room. The light projection apparatus is configured to generate a light projection that defines an areal region in the room with light of a predetermined wavelength characteristic. The system has a large number of optical detectors for mounting in the areal region that are configured to detect light with the wavelength characteristic, and dependent thereon, from the detected light, to generate at least one detector signal. The system has at least one computing unit that is configured, dependent upon the at least one detector signal, to recognize a coverage of at least a portion of the large number of optical detectors by an object and, dependent upon the recognized coverage, to initiate a safety and/or warning measure.

A computing unit may be understood, for example, to be a data processing device that contains a processing circuit. The computing unit may thus process, for example, data to carry out computation operations. This also covers, where relevant, operations to carry out indicated access operations on a data structure (e.g., a look-up table (LUT)).

The computing unit may include, for example, one or more computers, one or more microcontrollers, and/or one or more integrated circuits (e.g., one or more application-specific integrated circuits (ASICs), one or more field-programmable gate arrays (FPGA), and/or one or more system on a chip (SoC) units). The computing unit may also contain one or more processors (e.g., one or more microprocessors, one or more central processing units (CPUs), one or more graphics processing units (GPUs), and/or one or more signal processors, such as, one or more digital signal processors (DSPs)). The computing unit may also include a physical or a virtual network of computers or others of the aforementioned units.

In different example embodiments, the computing unit includes one or more hardware and/or software interfaces and/or one or more storage units.

A storage unit may be configured as a volatile data store (e.g., as a dynamic random access memory, DRAM, or as a static random access memory, SRAM, or as a non-volatile data store, such as, a read-only memory, ROM, as a programmable read-only memory, PROM, as an erasable programmable read-only memory, EPROM, as an electrically erasable programmable read-only memory, EEPROM, as a flash memory or flash-EEPROM, as a ferroelectric random access memory, FRAM, as a magnetoresistive random access memory, MRAM, or as a phase-change random access memory, PCRAM).

In some embodiments of the system, the room or portions of the room and/or the medical technology apparatus may be configured as a portion of the system. For example, the light projection apparatus is mounted in the room (e.g., on a ceiling or a side wall of the room or on an object in the room or on the medical technology apparatus itself). For example, the optical detectors of the large number of optical detectors are mounted in the areal region (e.g., integrated into a floor).

According to at least one embodiment, the light projection apparatus is configured as a laser projection apparatus and therefore has one or more laser light sources (e.g., laser diodes) in order to generate the light and, accordingly, the light projection.

By this, a particularly simple definition of the wavelength characteristic is enabled, since the wavelength characteristic may be defined by one or more emission wavelengths of the laser light source or sources. In addition, with a suitable adaptation of the optical detectors, the selectivity of the optical detectors may be more easily achieved.

According to at least one embodiment, the light projection apparatus is configured to generate the light at least partially in a visible spectral region.

It is achieved in this way, for example, that persons in the room may intuitively recognize where the areal region that potentially is to be avoided is situated. It is also possible that different portions of the areal region or different areal regions are illuminated with light of different colors in order thereby, for example, to emphasize or define different criticality stages.

According to at least one embodiment, each optical detector of the large number of optical detectors includes one or more photodiodes or an array of photodiodes.

Further embodiments of the system for monitoring a room follow directly from the different configurations of the method according to the present embodiments for monitoring a room, and vice versa. For example, individual features and corresponding explanations and advantages relating to the different embodiments of the method according to the present embodiments may be transferred analogously to corresponding embodiments of the system according to the present embodiments. For example, the system according to the present embodiments for carrying out a method according to the present embodiments is configured or programmed. For example, the system according to the present embodiments carries out the method according to the present embodiments.

Further features of the present embodiments are disclosed in the claims, the drawings, and the description of the drawings. The features and combinations of features mentioned in the description above and the following features and combinations of features mentioned in the description of the drawings and/or shown in the drawings alone may be included by the present embodiments not only in the respective combinations given, but also in other combinations. For example, embodiments and combinations of features that do not have all the features of an originally formulated claim are also included by the present embodiments. Further, embodiments and combinations of features that go beyond or deviate from the combinations of features represented by the back-references in the claims may also be included by the present embodiments.

The present embodiments will now be described in greater detail by reference to specific example embodiments and the associated schematic drawings. In the figures, the same or functionally equivalent elements may have been given the same reference signs. The description of the same or functionally equivalent elements will, where relevant, not necessarily be repeated in relation to different drawings.

10

Figure 2:
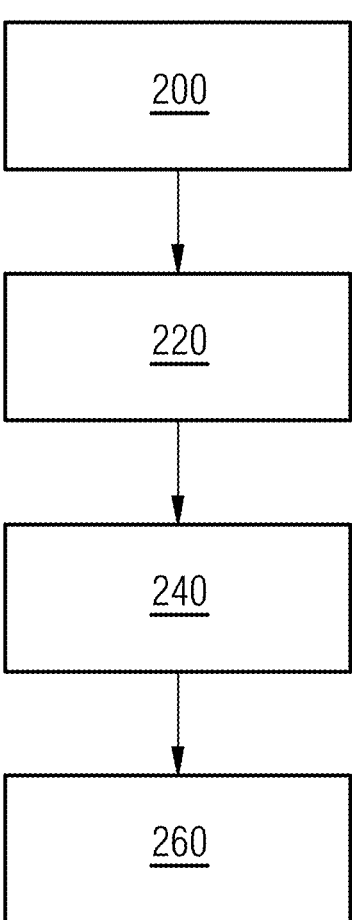

FIG. 2 shows a schematic flow diagram of an example embodiment of a method for monitoring a room with a medical technology apparatus.

DETAILED DESCRIPTION

Figure 1:
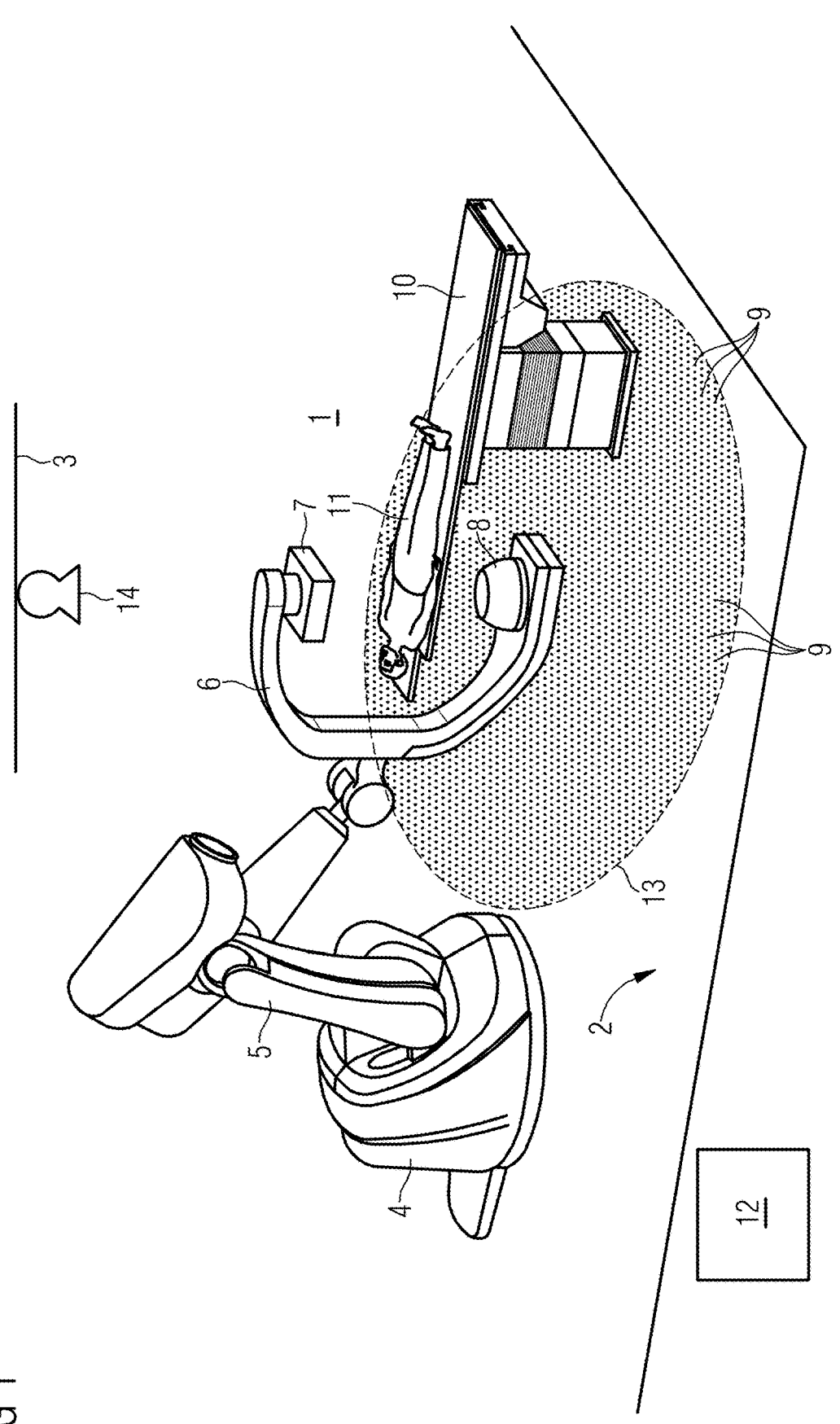
FIG. 1 shows a schematic representation of a room with an example embodiment of a system for monitoring the room.

FIG. 1 shows a schematic representation of a room with a medical technology apparatus 4 and an example embodiment of a system 1 for monitoring the room. The system 1 is configured to carry out a method according to the present embodiments. FIG. 2 shows a schematic flow diagram of an example embodiment of such a method.

The medical technology apparatus 4 is shown in FIG. 1, by way of example, as a C-arm X-ray system with a stand 5, a C-arm 6, an X-ray detector 7 arranged on the C-arm 6, and an X-ray source 8 arranged opposite the X-ray detector 7 on the C-arm 6. Further, by way of example, a patient table 10 with a patient 11 is shown. The patient 11, for example, may be examined and/or treated by the medical technology apparatus 4. However, the system 1 and the method according to the present embodiments are not restricted to the specific embodiment of the medical technology apparatus 4.

The system 1 has at least one computing unit 12 that may be arranged in the room, but may also be situated outside or partially outside the room. The system has a light projection apparatus 14 that is mounted in the room (e.g., on the ceiling 3 of the room). The light projection apparatus 14 may be configured, for example, as a laser projector.

In the method act 200, the light projection apparatus 14 may generate a light projection, for example, with light of a predetermined wavelength characteristic, for example, of a pre-determined wavelength or color that defines an areal region 13 in the room, for example, on a base 2 of the room.

The system 1 has a large number of optical detectors 9 (e.g., photodiodes that are arranged in the areal region 13, such as integrated into the base 2 or arranged on the base 2). The optical detectors 9 are configured to detect light with the wavelength characteristic.

In the method act 220, the optical detectors 9 each generate a detector signal dependent upon (e.g., based on) the light that is incident upon the respective active surface (e.g., the light generated by the light projection apparatus 14), provided the corresponding optical detectors 9 are not covered.

In the method act 240, dependent upon (e.g., based on) the detector signals, the at least one computing unit 12 may recognize a coverage of at least a portion of the large number of optical detectors 9 by an object. For example, an amplitude of one of the detector signals indicates the energy of the light that is incident upon the active surface of the respective optical detector 9. If this energy is lower than a particular threshold value, then a coverage of the optical detector may therefore be assumed.

In the method act 260, the at least one computing unit then initiates a safety and/or warning measure dependent upon the coverage recognized.

The safety and/or warning measure may include, for example, the braking or cessation of a moving component of the medical technology apparatus 4 (e.g., in the example of FIG. 1, the C-arm 6 or the stand 5 or another movable object, such as, in the example of FIG. 1, the patient table 10). Alternatively or additionally, an acoustic warning message and/or a visual warning message may also be output.

The safety and/or warning measure may be initiated, for example, when the coverage of the areal region has been ascertained based on the at least one detector signal. The areal region may signify, for example, a movement region of the medical technology apparatus 4 (e.g., of a movable component of the medical technology apparatus 4; in the example of FIG. 1, of the C-arm 6 or the stand 5, such as a region in which an increased risk of a collision exists). The areal region may also signify a region in which an elevated radiation burden is to be expected. The areal region may also signify a sterile region. In these cases, via the safety and/or warning measure, the risk of a collision, the risk of an elevated radiation burden, and/or the risk of a contamination of the sterile region may be reduced.

It is also possible that the safety and/or warning measure is initiated when the coverage of the areal region has not been ascertained based on the at least one detector signal, for example, when according to a predetermined room model of the room, in a normal case, such a coverage by (e.g., a static object in the room) is to be expected.

In different embodiments, it is also possible that the areal region (e.g., its position and/or shape) changes dynamically (e.g., time-dependently using the light projection apparatus 14), for example, controlled by the at least one computing unit 12, or a movement of the components of the medical technology apparatus 4 is tracked. In this way, account may be taken of the circumstance that, during a movement of a component of the medical technology apparatus 4, the region in which the collision risk is particularly high or in which the radiation burden is particularly high may possibly also change.

The present embodiments may similarly be extended also for a plurality of light projections, areal regions, and so forth. Different areal regions or their respective coverage may also be handled differently.

The present embodiments may enhance safety in the room (e.g., in an operating room). For this purpose, light markings (e.g., on the base) may be used in order to monitor reliably the encroachment upon the areal region defined thereby and, if relevant, to warn personnel.

In order to generate the light projection, in different embodiments, spectral laser projectors are used, and correspondingly, wavelength-sensitive sensors may be used as optical detectors.

Through the integration of the optical detectors in the base 2 of the room, gaps and cracks or suchlike that may possibly lead to the contamination of sterile regions may also be avoided.

Via the present embodiments, the monitoring (e.g., the detection of the coverage) may also be realized in different embodiments, independently of devices to be carried by persons.

In different embodiments, a projector installed on the ceiling may be used to signify regions with different risk levels on the laboratory floor (e.g., green for low, yellow for moderate, and red for high risk of a collision or corresponding radiation risk). The optical detectors that react adaptively to the expected wavelength of the projector may be installed in the base. If a person or other object hinders the path of the light, a safety and/or warning measure may be triggered.

In different embodiments, the safety and/or warning measure is only triggered when the object or the person who enters a risk region moves. This may be determined by evaluating the sequence and/or number of the covered optical detectors. In this way, static objects (e.g., in a risk region) may be treated as unproblematic.

Independent of the grammatical term usage, individuals with male, female, or other gender identities are included within the term.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for monitoring a room having a medical technology apparatus, the method comprising:
   generating, by a light projector, a light projection that defines an areal region in the room with light of a predetermined wavelength characteristic;
   generating at least one detector signal using a number of optical detectors that are each mounted in the areal region and are configured for detecting light having the predetermined wavelength characteristic;
   recognizing, by a processor, a coverage of at least a portion of the number of optical detectors by an object based on the at least one detector signal; and
   initiating, by the processor, a safety, warning, or safety and warning measure based on the recognized coverage.

2. The method of claim 1, wherein the safety, warning, or safety and warning measure comprises:
   a cessation or braking of a movement of a component of the medical technology apparatus;
   a cessation of a generation of ionizing radiation by the medical technology apparatus; or
   a combination thereof.

3. The method of claim 1, wherein the safety, warning, or safety and warning measure comprises:
   a bringing of a component of the medical technology apparatus into a predefined safe position or location;
   an output of an acoustic warning message, a visual warning message, or the acoustic warning message and the visual warning message; or
   a combination thereof.

4. The method of claim 1, wherein a form, a size, a position, or any combination thereof of the areal region in the room is changed dependent upon a state of the medical technology apparatus.

5. The method of claim 1, further comprising detecting a movement of the object based on the at least one detector signal; and
   wherein the safety, warning, or safety and warning measure is initiated based on the detected movement.

6. The method of claim 5, wherein the safety, warning, or safety and warning measure is initiated if it is ascertained, based on the detected movement, that the object moves in a direction of a predetermined critical region.

7. The method of claim 1, further comprising providing a room model of the room,
   wherein the safety, warning, or safety and warning measure is initiated based on the room model.

8. The method of claim 7, wherein the room model includes a position of the medical technology apparatus, a position of at least one further object, or the position of the medical technology apparatus and the position of the at least one further object in the room, and wherein the safety, warning, or safety and warning measure is initiated based on the position of the medical technology apparatus, the position of the at least one further object, or the position of the medical technology apparatus and the position of the at least one further object.

9. The method of claim 8, wherein the room model includes a movement region of the medical technology apparatus, a movement region of the at least one further object, or the movement region of the medical technology apparatus and the movement region of the at least one further object; and wherein the safety, warning, or safety and warning measure is initiated based on the movement region of the medical technology apparatus, the movement region of the at least one further object, or the movement region of the medical technology apparatus and the movement region of the at least one further object.

10. The method of claim 1, further comprising:

based on the recognized coverage, activating a sensor that is arranged in the areal region or in a predetermined further areal region; and generating, by the sensor, a sensor signal based on a presence of the object in a detection region of the further sensor, wherein the safety, warning, or safety and warning measure is initiated based on the sensor signal.

11. The method of claim 1, wherein light incident upon the number of optical detectors is filtered according to the predetermined wavelength characteristic.

12. The method of claim 1, wherein the areal region corresponds to:

a movement region of the medical technology apparatus;
a predetermined region of elevated radiation burden;
a predetermined sterile region; or
a combination thereof.

13. The method of claim 1, wherein an identity of the object is ascertained, and the safety, warning, or safety and warning measure is initiated based on the ascertained identity.

14. A system for monitoring a room having at least one medical technology apparatus, the system comprising:

a light projector that is mountable in the room, the light projector being configured to generate a light projection that defines an areal region in the room with light of a predetermined wavelength characteristic;

a number of optical detectors that are mountable in the areal region, the number of optical detectors being configured to:

detect light with the predetermined wavelength characteristic; and based on the detected light, generate at least one detector signal; and at least one processor configured to:

based on the at least one detector signal, recognize a coverage of at least a portion of the number of optical detectors by an object; and based on the recognized coverage, initiate a safety, warning, or safety and warning measure.

15. The system of claim 14, wherein:

the light projector is configured for mounting on a ceiling or on a side wall of the room;

the number of optical detectors are configured for mounting in a base of the room;

the light projector is configured as a laser projection apparatus;

the light projector is configured to generate the light at least partially in a visible spectral region; or any combination thereof.

* * * * *